United States Patent
Dobner et al.

(10) Patent No.: US 10,022,714 B2
(45) Date of Patent: Jul. 17, 2018

(54) CATALYST AND METHOD FOR PRODUCING MALEIC ANHYDRIDE

(71) Applicant: BASF SE, Ludwigshafen (DE)

(72) Inventors: Cornelia Katharina Dobner, Ludwigshafen (DE); Stefan Altwasser, Wachenheim (DE); Hagen Wilmer, Ludwigshafen (DE); Frank Rosowski, Mannheim (DE)

(73) Assignee: BASF SE, Ludwigshafen am Rhein (DE)

( * ) Notice: Subject to any disclaimer, the term of this patent is extended or adjusted under 35 U.S.C. 154(b) by 155 days.

(21) Appl. No.: 14/823,292

(22) Filed: Aug. 11, 2015

(65) Prior Publication Data
US 2015/0343433 A1    Dec. 3, 2015

Related U.S. Application Data

(62) Division of application No. 13/141,139, filed on Jun. 21, 2011, now Pat. No. 9,138,729.

(30) Foreign Application Priority Data

Dec. 22, 2008  (EP) ..................................... 08172635
Dec. 21, 2009  (WO) ................. PCT/EP2009/067661

(51) Int. Cl.
*B01J 35/02*    (2006.01)
*B01J 35/10*    (2006.01)
(Continued)

(52) U.S. Cl.
CPC .......... *B01J 35/023* (2013.01); *B01J 27/198* (2013.01); *B01J 35/02* (2013.01); *B01J 35/026* (2013.01);
(Continued)

(58) Field of Classification Search
CPC ..... C07C 57/145; B01J 27/198; B01J 35/002; B01J 35/023; B01J 35/1042;
(Continued)

(56) References Cited

U.S. PATENT DOCUMENTS

| 4,283,307 A | 8/1981 | Barone et al. |
| 4,795,818 A | 1/1989 | Becker et al. |

(Continued)

FOREIGN PATENT DOCUMENTS

| EP | 1120390 A1 | 8/2001 |
| EP | 1261424 A1 | 12/2002 |

(Continued)

*Primary Examiner* — Camie S Thompson
(74) *Attorney, Agent, or Firm* — Drinker Biddle & Reath LLP

(57) ABSTRACT

The invention relates to a catalyst molded body for preparing maleic anhydride by gas-phase oxidation of a hydrocarbon having at least four carbon atoms using a catalytically active composition containing vanadium, phosphorus and oxygen. The shaped catalyst body has an essentially cylindrical body having a longitudinal axis. The cylindrical body has at least two parallel internal holes which are essentially parallel to the cylinder axis of the body and go right through the body. The catalyst molded body has a large outer surface area, a lower pressure loss and sufficient mechanical stability.

11 Claims, 1 Drawing Sheet

(51) Int. Cl.
   *B01J 27/198*   (2006.01)
   *B01J 37/00*    (2006.01)
   *C07C 51/215*   (2006.01)
   *B01J 35/00*    (2006.01)

(52) U.S. Cl.
   CPC ....... *B01J 35/1038* (2013.01); *B01J 35/1042* (2013.01); *B01J 37/0009* (2013.01); *B01J 37/0018* (2013.01); *C07C 51/215* (2013.01); *B01J 35/002* (2013.01); *Y10T 428/2975* (2015.01)

(58) Field of Classification Search
   CPC ...... B01J 35/1038; B01J 35/02; B01J 35/026; B01J 35/10; Y10T 428/2975
   USPC .......................... 428/398; 502/209; 549/256
   See application file for complete search history.

(56) References Cited

U.S. PATENT DOCUMENTS

| | | | |
|---|---|---|---|
| 4,933,312 A | 6/1990 | Haddad et al. | |
| 5,095,125 A | 3/1992 | Haddad et al. | |
| 5,137,860 A | 8/1992 | Ebner et al. | |
| 5,158,923 A | 10/1992 | Barone | |
| 5,168,090 A | 12/1992 | Ebner et al. | |
| 5,275,996 A | 1/1994 | Andrews et al. | |
| 5,296,436 A | 3/1994 | Bortinger | |
| 5,651,722 A | 6/1997 | Mitchell et al. | |
| 5,986,152 A * | 11/1999 | Muller | B01J 23/83 502/302 |
| 6,812,351 B2 | 11/2004 | Weiguny et al. | |
| 2001/0011149 A1 | 8/2001 | MelBner et al. | |
| 2003/0114688 A1 * | 6/2003 | Weiguny | B01J 23/002 549/259 |
| 2004/0014990 A1 | 1/2004 | Storck et al. | |
| 2005/0222435 A1 * | 10/2005 | Weiguny | B01J 23/002 549/259 |
| 2008/0177105 A1 | 7/2008 | Raichle et al. | |
| 2008/0214863 A1 | 9/2008 | Cremer et al. | |
| 2008/0307648 A1 | 12/2008 | Cremer et al. | |
| 2008/0312477 A1 | 12/2008 | Raichle et al. | |
| 2009/0306410 A1 | 12/2009 | Brandstadter et al. | |
| 2010/0069659 A1 | 3/2010 | Raichle et al. | |
| 2010/0069660 A1 | 3/2010 | Raichle et al. | |
| 2011/0026740 A1 | 2/2011 | Dobner et al. | |
| 2011/0034707 A1 | 2/2011 | Wilmer et al. | |
| 2011/0118487 A1 | 5/2011 | Abdallah et al. | |
| 2011/0257414 A1 | 10/2011 | Dobner et al. | |
| 2012/0071671 A1 | 3/2012 | Karpov et al. | |
| 2012/0077998 A1 | 3/2012 | Seeber et al. | |
| 2012/0149919 A1 | 6/2012 | Altwasser et al. | |
| 2012/0271567 A1 | 10/2012 | Da Pont et al. | |

FOREIGN PATENT DOCUMENTS

| | | |
|---|---|---|
| EP | 1386664 A1 | 2/2004 |
| JP | 6170239 A | 6/1994 |
| WO | WO-95/26817 A1 | 10/1995 |
| WO | WO-95/29006 A1 | 11/1995 |
| WO | WO-97/12674 A1 | 4/1997 |
| WO | WO-01/058245 A1 | 9/2001 |
| WO | WO-02/34387 A1 | 5/2002 |
| WO | WO-03/078057 | 9/2003 |
| WO | WO-2007/051802 A1 | 5/2007 |
| WO | WO-2008/087116 A1 | 7/2008 |

* cited by examiner

CATALYST AND METHOD FOR PRODUCING MALEIC ANHYDRIDE

CROSS REFERENCE TO RELATED APPLICATION

This application is a divisional of U.S. Ser. No. 13/141,139 filed Jun. 21, 2011 which is incorporated by reference in its entirety for all useful purposes. U.S. Ser. No. 13/141,139 is a national stage entry of Application No. PCT/EP2009/067661 filed Dec. 21, 2009. This application and Application No. PCT/EP2009/067661 claim the benefit of European Application No. 08172635.8 filed Dec. 22, 2008.

BACKGROUND OF THE INVENTION

The present invention relates to a catalyst for preparing maleic anhydride (MAn) by gas-phase partial oxidation. The invention further relates to a process for preparing maleic anhydride using the catalyst of the invention.

To carry out a heterogeneously catalyzed gas-phase oxidation, a mixture of an oxygen-comprising gas, for example air, and the hydrocarbon to be oxidized is generally passed through a plurality of tubes which are arranged in a reactor and in which a bed of shaped catalyst bodies is present.

Heterogeneous catalysts based on vanadyl pyrophosphate $(VO)_2P_2O_7$ (known as VPO catalysts) are used in the industrial oxidation of hydrocarbons such as n-butane to maleic anhydride. The rate of this heterogeneously catalyzed oxidation in the gas phase is limited by internal transport influences. Here, it is not the diffusion of reactants to the outer surface of the catalyst but the speed of diffusion into the pore structure of the catalyst which is the rate limiting step for the reaction.

The mass transfer limitation can be reduced by increasing the porosity of the catalyst. For this purpose, pore formers, i.e. organic compounds which burn out during later heating, are added to the catalytically active composition. However, this optimization is subject to limits because excessively porous shaped catalyst bodies no longer have sufficient mechanical stability.

A further possible way of improving these catalysts is optimization of the geometry of the shaped bodies. This determines both the external surface area of the catalyst and the resistance to the gas flowing through the bed and thus the pressure drop which has to be overcome between the reactor inlet and the reactor outlet caused by the catalyst particles. Although the use of relatively small catalyst particles increases the external surface area and thus the activity of the catalyst, the pressure drop increases greatly at the same time. In addition, variation of the geometry of the shaped bodies is subject to limits in that the catalyst obtained should have sufficient mechanical stability and no excessive fracture should occur, e.g. on filling the reaction tubes. Geometries having parts which project a long way, thin struts and the like generally have unsatisfactory mechanical stability.

A catalyst geometry which has a large external surface area and displays a low pressure drop and satisfactory mechanical stability is therefore sought.

U.S. Pat. No. 4,283,307 discloses an oxidation catalyst for the partial oxidation of n-butane to MAn in the form of a pellet having a central hole.

U.S. Pat. No. 5,168,090 describes shaped catalyst bodies for preparing MAn whose external surface has at least one hollow space and whose geometric volume corresponds to from 30 to 67% of the volume of the hollow-space-free geometric shape and which have a ratio of the external geometric surface area to the geometric volume of at least 20 $cm^{-1}$. Specifically, U.S. Pat. No. 5,168,090 discloses cylinders having 3 equidistant grooves in the external surface which run parallel to the axis of the cylinder.

WO 01/68245 discloses a catalyst for preparing maleic anhydride by heterogeneously catalyzed gas-phase oxidation, which catalyst has an essentially hollow cylindrical structure which has a particular ratio of the height to the diameter of the through-hole and a particular ratio of the geometric surface area to the geometric volume.

WO 03/078057 describes a catalyst for preparing maleic anhydride, which catalyst comprises a catalytically active composition comprising vanadium, phosphorus and oxygen and has an essentially hollow cylindrical structure and a geometric density $d_p$ which satisfies particular conditions.

WO 2007/051 602 describes shaped catalyst bodies for preparing maleic anhydride, where the geometric base body enveloping the shaped catalyst body is a prism and the shaped catalyst body is provided with three through-holes. The shaped catalyst body should have a triangular cross section with rounded corners.

EP-A 1 120 390 describes a process for preparing 1,2-dichloroethane by oxychlorination of ethene over a bed of catalyst particles. The catalyst particles can be present as cylinders having axial holes.

JP 06-170239 discloses shaped catalyst bodies having a cylindrical body and at least two holes for the synthesis of unsaturated aldehydes and carboxylic acids.

BRIEF SUMMARY OF THE INVENTION

It is an object of the present invention to provide a shaped catalyst body for the preparation of MAn, which has a large external surface area and displays a low pressure drop and satisfactory mechanical stability. In particular, it is an object of the invention to provide a shaped catalyst body which makes possible a high yield in the gas-phase partial oxidation and a high selectivity to MAn at a low pressure drop.

According to the invention, the object is achieved by a shaped catalyst body for preparing maleic anhydride by gas-phase oxidation of a hydrocarbon having at least four carbon atoms using a catalytically active composition comprising vanadium, phosphorus and oxygen, where the shaped catalyst body has an essentially cylindrical body having a longitudinal axis, wherein the cylindrical body has at least two, e.g. from 2 to 5, parallel internal holes which are essentially parallel to the cylinder axis of the body and go right through the body.

DETAILED DESCRIPTION OF THE INVENTION

Figure 1:
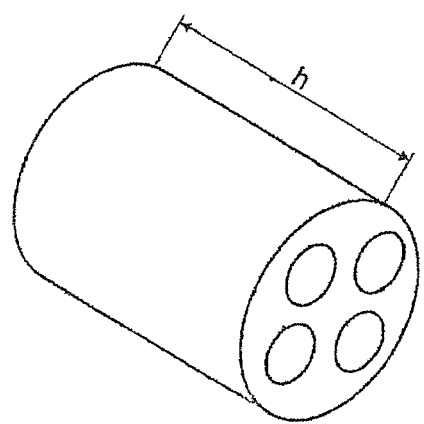
FIG. 1 shows a view of a shaped catalyst body according to the invention having four internal holes.

The shaped catalyst body has an essentially cylindrical body, i.e. a body having a circular cross section and flat parallel end faces. The term "essentially" indicates that deviations from the ideal geometry, for example slight deformations of the circular structure, end faces which are not flat and parallel, chipped corners and edges, surface roughness or notches in the cylindrical surface, the end faces or the internal surface of the through-holes are also comprised in the case of the shaped catalyst body of the invention.

The cylindrical body particularly preferably has four internal holes.

The internal holes preferably have a round or oval cross section, in particular a round cross section. In general, all internal holes have the same cross section.

In preferred embodiments, the central axes of the internal holes are located equidistantly on a cylindrical surface which is concentric with the surface of the cylindrical body. The ratio of the diameter $d_2$ of an internal hole to the external diameter $d_1$ of the cylindrical body is preferably from 0.2 to 0.35. The ratio of the diameter $d_3$ of the cylindrical surface on which the central axes of the internal holes are located to the external diameter $d_1$ of the cylindrical body is preferably 0.53 to 0.60.

The use of two or more internal holes enables the area formed by the surfaces of the internal holes to be increased greatly compared to a simple hollow cylinder having a comparable proportion of the hollow space. In preferred embodiments, the sum of the surfaces of the internal holes is equal to or greater than the external surface of the cylindrical body.

To obtain satisfactory mechanical stability, preference is given to both the smallest distance between the internal holes and also the smallest distance from the internal holes to the external surface of the body being in each case at least 6%, in particular at least 7%, of the diameter $d_1$ of the cylindrical body.

The ratio of the height h of the cylindrical body to the diameter $d_2$ of the internal holes is preferably not more than 3.5, in particular from 2.2 to 3.4.

The ratio of the geometric surface area $A_{geo}$ to the geometric volume $V_{geo}$ is preferably at least 2.0 mm$^{-1}$, e.g. from 2.05 to 2.6 mm$^{-1}$, preferably from 2.1 to 2.4 mm$^{-1}$. The geometric surface area $A_{geo}$ and the geometric volume $V_{geo}$ is derived from the external, macroscopic dimensions of the shaped catalyst body taking into account the external diameter $d_1$, the height h and the diameter $d_2$ and number of the internal holes.

The ratio of the geometric volume $V_{geo}$ of the cylindrical body to the theoretical volume $V_{overall}$ of a corresponding solid cylinder having the same height h and the same external diameter $d_1$ is preferably not more than 0.85, in particular from 0.55 to 0.72.

In general, the external diameter $d_1$ of the cylindrical body is from 3 to 10 mm, preferably from 4 to 8 mm, in particular from 5 to 7 mm, the height h of the cylindrical body is from 1 to 10 mm, preferably from 2 to 6 mm, in particular from 3 to 5 mm, and the diameter of each internal hole $d_2$ is from 0.5 to 4 mm, preferably from 1 to 3 mm.

The shaped catalyst body is preferably porous and in particular has a specific pore volume of at least 0.30 ml/g, particularly preferably at least 0.35 ml/g, e.g. from 0.38 to 0.50 ml/g. The specific pore volume PV is the (integrated) specific pore volume determined by mercury porosimetry in accordance with DIN 66133.

The shaped catalyst body of the invention can be an all-active catalyst or a mixed catalyst. For the purposes of the present invention, an all-active catalyst is a shaped body which consists essentially completely of the catalytically active composition. A mixed catalyst is a shaped body which comprises the catalytically active composition in dilute form in a mixture with a support material. Suitable support materials for the mixed catalysts are, for example, aluminum oxide, silicon dioxide, aluminosilicates, zirconium dioxide, titanium dioxide or mixtures thereof.

To produce all-active or mixed catalysts, a catalytically active composition or a precursor composition which can be converted into a catalytically active form by calcination, optionally in a mixture with a pulverulent inert support, is shaped to give a shaped catalyst body according to the invention.

Pore formers can be added to the composition to be shaped. Pore formers are materials which are used to produce porous shaped bodies in a targeted manner. In general, they are components which comprise carbon, hydrogen, oxygen and/or nitrogen and are added before shaping of the catalyst and are predominantly removed again by sublimation, decomposition and/or vaporization during the subsequent activation of the catalyst. The finished catalyst can comprise residues or decomposition products of the pore former. Suitable pore formers are, for example, fatty acids such as palmitic acid or stearic acid, dicarboxylic acids such as oxalic acid or malonic acid, cyclodextrins or polyethylene glycols. The use of malonic acid is preferred. If used, the pore former is preferably used in an amount of from 16 to 40 parts by weight, in particular from 20 to 25 parts by weight, per 100 parts by weight of the catalytically active composition.

The shaped catalyst bodies of the invention advantageously have a BET surface area of more than 15 m$^2$/g, preferably from >15 to 50 m$^2$/g and in particular from >15 to 40 m$^2$/g. They advantageously have a pore volume of more than 0.1 ml/g, preferably from 0.15 to 0.6 ml/g and in particular from 0.3 to 0.5 ml/g.

Shaping is preferably carried out by tableting. Tableting is a process of press agglomeration. Here, a pulverulent or previously agglomerated bulk material is introduced into a pressing tool having a die between two punches and compacted by uniaxial compression and shaped to give a solid compact. This operation is divided into four parts: metered introduction, compaction (elastic deformation), plastic deformation and ejection. Tableting is carried out, for example, on rotary presses or eccentric presses.

To form the internal holes, the upper punch and/or lower punch has projecting pins. It is also possible to provide the pressing punches with a plurality of movable pins, so that a punch can, for example, be made up of five part punches ("ring punch" having four "holes" and four pins).

The pressing force during tableting effects compaction of the bulk material. In practice, it has been found to be useful to set the lateral compressive strength of the shaped bodies in a targeted manner by selection of the appropriate pressing force and to check this by random sampling. For the purposes of the present invention, the lateral compressive strength is the force which fractures the shaped catalyst body located between two flat parallel plates, with the two flat parallel end faces of the cylindrical body being at right angles to the flat parallel plates.

For tableting, it is possible to make concomitant use of tableting aids such as graphite or magnesium stearate. The use of a graphite having a specific surface area of from 0.5 to 5 m$^2$/g and a particle diameter $d_{50}$ of from 40 to 200 μm, as described in WO 2008/087116, is preferred.

As an alternative to tableting, mention may be made by way of example of extrusion. In this variant, the bulk material is, for example, mixed with liquid to give an extrudable composition. This can be extruded to give an extrudate having a plurality of channels in the interior and the extrudate can be cut into cylindrical pieces.

The catalytically active composition comprises vanadium, phosphorus and oxygen. The atomic ratio of phosphorus/vanadium is generally from 0.9 to 1.5, preferably from 0.9 to 1.2, in particular from 1.0 to 1.1. The average oxidation state of the vanadium is preferably from +3.9 to +4.4 and preferably from 4.0 to 4.3. Suitable active compositions are described, for example, in the patent documents U.S. Pat. No. 5,275,996, U.S. Pat. No. 5,641,722, U.S. Pat. No. 5,137,860, U.S. Pat. No. 5,095,125 or U.S. Pat. No. 4,933,312.

The catalysts of the invention can further comprise promoters. Suitable promoters are the elements of groups 1 to 15 of the Periodic Table and compounds thereof. Suitable promoters are, for example, described in the publications WO 97/12674 and WO 95/26817 and in the patents U.S. Pat. No. 5,137,860, U.S. Pat. No. 5,296,436, U.S. Pat. No. 5,158,923 and U.S. Pat. No. 4,795,818. Compounds of the elements cobalt, molybdenum, iron, zinc, hafnium, zirconium, lithium, titanium, chromium, manganese, nickel, copper, boron, silicon, antimony, tin, niobium and bismuth, particularly preferably molybdenum, iron, zinc, antimony, bismuth, lithium, are preferably used as promoters. The promoted catalysts of the invention can comprise one or more promoters. The total content of promoters in the finished catalyst is generally not more than about 5% by weight, in each case calculated as oxide. Preference is given to compositions which do not comprise any promoters and those which comprise iron or molybdenum as promoter.

The main steps of the preferred catalyst production with formation of a precursor powder, shaping and subsequent calcination are as follows.

(a) Reaction of a pentavalent vanadium compound with an organic, reducing solvent in the presence of a phosphorus compound with heating. This step can optionally be carried out in the presence of a dispersed, pulverulent support material. Reaction without addition of support material is preferred.

(b) Isolation of the vanadium-, phosphorus-, oxygen-comprising catalyst precursor formed ("VPO precursor"), e.g. by filtration or evaporation.

(c) Drying of the VPO precursor and preferably initial preactivation by heating at a temperature of from 250 to 350° C. Pulverulent support material and/or a pore former, for example stearic acid, cellulose or paraffins, can then be added to the dried and preferably heat-treated VPO precursor powder.

(d) Shaping by conversion into the structure according to the invention. Shaping is preferably carried out by tableting, preferably with prior mixing with a lubricant such as graphite.

(e) Preactivation of the shaped VPO precursor by heating in an atmosphere comprising oxygen ($O_2$), hydrogen oxide ($H_2O$) and/or inert gas.

The mechanical and catalytic properties of the catalyst can be influenced by appropriate combinations of temperatures, treatment times and gas atmospheres matched to the respective catalyst system.

As pentavalent vanadium compounds, it is possible to use oxides, acids and inorganic and organic salts which comprise pentavalent vanadium, or mixtures thereof. Preference is given to using vanadium pentoxide ($V_2O_5$), ammonium metavanadate ($NH_4VO_3$) and ammonium polyvanadate (($NH_4)_2N_6O_{16}$), in particular vanadium pentoxide ($V_2O_5$). The pentavalent vanadium compounds present as solids are used in the form of a powder, preferably in a particle size range from 50 to 500 µm.

As phosphorus compounds, it is possible to use phosphorus compounds having a reducing action, for example phosphorous acid, and also pentavalent phosphorus compounds, for example phosphorus pentoxide ($P_2O_5$), orthophosphoric acid ($H_3PO_4$), pyrophosphoric acid ($H_4P_2O_7$), polyphosphoric acids of the general formula $H_{n+2}P_nO_{3n+1}$ where n≥3 or mixtures thereof. Preference is given to using pentavalent phosphorus compounds. The content of the compounds and mixtures mentioned is usually reported in % by weight based on $H_3PO_4$. Preference is given to using from 80 to 110% strength $H_3PO_4$, particularly preferably from 95 to 110% strength $H_3PO_4$ and very particularly preferably from 100 to 105% strength $H_3PO_4$.

As solvent having a reducing action, preference is given to using a primary or secondary, acyclic or cyclic, unbranched or branched, saturated alcohol having from 3 to 6 carbon atoms or a mixture thereof. Preference is given to using a primary or secondary, unbranched or branched $C_3$-$C_6$-alkanol or cyclopentanol or cyclohexanol.

Suitable alcohols which may be mentioned are n-propanol (1-propanol), isopropanol (2-propanol), n-butanol (1-butanol), sec-butanol (2-butanol), isobutanol (2-methyl-1-propanol), 1-pentanol, 2-pentanol, 3-pentanol, 2-methyl-1-butanol, 3-methyl-1-butanol, 3-methyl-2-butanol, 2,2-dimethyl-1-propanol, 1-hexanol, 2-hexanol, 3-hexanol, 2-methyl-1-hexanol, 3-methyl-1-pentanol, 4-methyl-1-pentanol, 3-methyl-2-pentanol, 4-methyl-2-pentanol, 2,2-dimethyl-1-butanol, 2,3-dimethyl-1-butanol, 3,3-dimethyl-1-butanol, 3,3-dimethyl-2-butanol, cyclopentanol, cyclohexanol and mixtures thereof.

Very particular preference is given to n-propanol (1-propanol), n-butanol (1-butanol), isobutanol (2-methyl-1-propanol), 1-pentanol, 2-methyl-1-butanol, 3-methyl-1-butanol and cyclohexanol, in particular isobutanol.

The components can be combined in various ways, for example in a stirred vessel. The amount of the solvent having a reducing action should be above the amount which is stochiometrically required for reduction of the vanadium from the oxidation state +5 to an oxidation state in the range from +3.5 to +4.5. In general, the amount of solvent having a reduction action to be added is at least such an amount that it is sufficient for slurrying the pentavalent vanadium compound so as to make intensive mixing with the phosphorus compound added possible.

The slurry is heated to convert the abovementioned compounds and form the catalyst precursor. The temperature range to be selected is dependent on various factors, in particular the reducing action and the boiling point of the components. In general, a temperature of from 50 to 200° C., preferably from 100 to 200° C., is set. The reaction at elevated temperature generally takes a number of hours.

Promoter compounds can be added at any point in time. Suitable promoter compounds are, for example, the acetates, acetylacetonates, oxalates, oxides or alkoxides of the abovementioned promoter metals, for instance cobalt acetate, cobalt(II) acetylacetonate, cobalt(II) chloride, molybdenum (VI) oxide, molybdenum(III) chloride, iron(III) acetylacetonate, iron(III) chloride, zinc(II) oxide, zinc(II) acetylacetonate, lithium chloride, lithium oxide, bismuth(III) chloride, bismuth(III) ethylhexanoate, nickel(II) ethylhexanoate, nickel(II) oxalate, zirconyl chloride, zirconium(IV) butoxide, silicon(IV) ethoxide, niobium(V) chloride and niobium (V) oxide.

After the abovementioned heat treatment is complete, the catalyst precursor formed is isolated, with a cooling phase and a storage or aging phase for the cooled reaction mixture optionally being able to be inserted before isolation. In the isolation step, the solid catalyst precursor is separated off from the liquid phase. Suitable methods are, for example, filtration, decantation or centrifugation. The catalyst precursor is preferably isolated by filtration.

The isolated catalyst precursor can be processed further with or without prior washing. The isolated catalyst precursor is preferably washed with a suitable solvent in order, for example, to remove residual agent having a reducing action (e.g. alcohol) or degradation products thereof which still adhere(s) to the catalyst precursor. Suitable solvents are, for example, alcohols (e.g. methanol, ethanol, 1-propanol, 2-propanol), aliphatic and/or aromatic hydrocarbons (e.g. pentane, hexane, petroleum spirit, benzene, toluene, xylenes), ketones (e.g. acetone, 2-butanone, 3-pentanone), ethers (e.g. 1,2-dimethoxyethane, tetrahydrofuran, 1,4-dioxane) or mixtures thereof. If the catalyst precursor is washed, preference is given to using 2-propanone and/or methanol and particularly preferably methanol.

After isolation of the catalyst precursor or after washing, the solid is generally dried.

Drying can be carried out under various conditions. In general, it is carried out under reduced pressure or atmospheric pressure. The drying temperature is generally from 30 to 250° C. Drying is preferably carried out at a pressure of from 1 to 30 kPa abs and a temperature of from 50 to 200° C. in an oxygen-comprising or oxygen-free gas atmosphere, for example air or nitrogen.

In a preferred embodiment of the shaping operation, the catalyst precursor powder is intensively mixed with from about 2 to 4% by weight of graphite and predensified. The predensified particles are tableted to give the shaped catalyst body.

In a further embodiment of the shaping operation, the catalyst precursor powder is intensively mixed with from about 2 to 4% by weight of graphite and additionally with from 5 to 40% by weight, in particular from 20 to 25% by weight, of a pore former and further treated and shaped as described above.

The shaped VPO precursor is preactivated (calcined) by heating in an atmosphere comprising oxygen ($O_2$), hydrogen oxide ($H_2O$) and/or inert gas in a temperature range from 250 to 600° C.

Suitable inert gases are, for example, nitrogen, carbon dioxide and noble gases.

The calcination can be carried out batchwise, for example in a shaft furnace, tray furnace, muffle furnace or oven, or continuously, for example in a rotary tube furnace, belt calcination furnace or rotary bulb furnace. It can comprise successive different sections in respect of the temperature, e.g. heating, holding of a constant temperature or cooling, and successive different sections in respect of the atmospheres, for example oxygen-comprising, water vapor-comprising, oxygen-free gas atmospheres. Suitable preactivation processes are described, for example, in the patents U.S. Pat. No. 5,137,860 and U.S. Pat. No. 4,933,312 and the publication WO 95/29006. Particular preference is given to continuous calcination in a belt calcination furnace having at least two, for example from two to ten, calcination zones which optionally have a different gas atmosphere and a different temperature. The mechanical and catalytic properties of the catalyst can be influenced and thus set in a targeted way by a suitable combination of temperatures, treatment times and gas atmospheres matched to the respective catalyst system.

Preference is given to a calcination in which the catalyst precursor is
(i) heated to a temperature of from 200 to 350° C. in an oxidizing atmosphere having an oxygen content of from 2 to 21% by volume in at least one calcination zone and maintained under these conditions until the desired average oxidation state of the vanadium has been attained; and
(ii) heated to a temperature of from 300 to 500° C. in a nonoxidizing atmosphere having an oxygen content of ≤0.5% by volume and a hydrogen oxide content of from 20 to 75% by volume in at least one further calcination zone and maintained under these conditions for ≥0.5 hour.

In step (i), the catalyst precursor is kept at a temperature of from 200 to 350° C. and preferably from 250 to 350° C. in an oxidizing atmosphere having a content of molecular oxygen of generally from 2 to 21% by volume and preferably from 5 to 21% by volume for a period of time which enables the desired average oxidation state of the vanadium to be established. In general, mixtures of oxygen, inert gases (e.g. nitrogen or argon), hydrogen oxide (water vapor) and/or air and also air are used in step (i). As far as the catalyst precursor conveyed through the calcination zone(s) is concerned, the temperature during the calcination step (i) can be kept constant or on average increase or decrease. Since step (i) is generally preceded by a heating phase, the temperature will in general firstly increase and then oscillate toward the desired final value. The calcination zone of step (i) is therefore generally preceded by at least one further calcination zone for heating up the catalyst precursor.

The period of time for which the heat treatment in step (i) is continued in the process of the invention should preferably be selected so that an average oxidation state of the vanadium of from +3.9 to +4.4, preferably from +4.0 to +4.3, is established.

Since determination of the average oxidation state of vanadium during calcination is extremely difficult for reasons of apparatus and time, the period of time required is advantageously determined experimentally in preliminary tests. In general, this is carried out using a series of measurements in which the samples are heat treated under defined conditions and are taken from the system after different times, cooled and analyzed to determine the average oxidation state of vanadium.

The time required in step (i) is generally dependent on the nature of the catalyst precursor, the temperature set and the gas atmosphere selected, in particular the oxygen content. In general, the time in step (i) extends to a period of over 0.5 hour and preferably over 1 hour. In general, a time of up to 4 hours, preferably up to 2 hours, is sufficient to set the desired average oxidation state. However, under some conditions (e.g. low range of the temperature interval and/or low content of molecular oxygen), a period of over 6 hours can be required.

In step (ii), the catalyst intermediate obtained is kept at a temperature of from 300 to 500° C. and preferably from 350 to 450° C. in a nonoxidizing atmosphere having a content of molecular oxygen of ≤0.5% by volume and of hydrogen oxide (water vapor) of from 20 to 75% by volume, preferably from 30 to 60% by volume, for a period of ≥0.5 hour, preferably from 2 to 10 hours and particularly preferably from 2 to 4 hours. The nonoxidizing atmosphere generally comprises, in addition to the hydrogen oxide mentioned, predominantly nitrogen and/or noble gases such as argon, but this does not constitute a restriction. Gases such as carbon dioxide are in principle also suitable. The nonoxidizing atmosphere preferably comprises ≥40% by volume of nitrogen. As far as the catalyst precursor conveyed through the calcination zone(s) is concerned, the temperature during the calcination step (ii) can be kept constant or on average increase or decrease. If step (ii) is carried out at a higher or lower temperature than step (i), there is generally a heating or cooling phase between the steps (i) and (ii), which is optionally implemented in a further calcination zone. To make improved separation from the oxygen-comprising atmosphere of step (i) possible, this further calcination zone between (i) and (ii) can, for example, be flushed with inert gas such as nitrogen. Step (ii) is preferably carried out at a temperature which is from 50 to 150° C. higher than that in step (i).

In general, the calcination comprises a further step (iii) which is to be carried out after step (ii) and in which the calcined catalyst precursor is cooled in an inert gas atmosphere to a temperature of ≤300° C., preferably from ≤200° C. and particularly preferably ≤150° C.

In the calcination according to the process of the invention, further steps are possible before, between and/or after steps (i) and (ii) or (i), (ii) and (iii). Without constituting a limitation, further steps which may be mentioned are, for example, changes in the temperature (heating, cooling), changes in the gas atmosphere (setting of a different gas atmosphere), further hold times, transfer of the catalyst intermediate into other apparatuses or interruption of the overall calcination operation.

Since the catalyst precursor is generally at a temperature of <100° C. before commencement of calcination, it usually has to be heated before step (i). Heating can be carried out using various gas atmospheres. Heating is preferably carried out in an oxidizing atmosphere as defined under step (i) or an inert gas atmosphere as defined under step (iii). The gas atmosphere can also be changed during the heating phase. Particular preference is given to heating up in the oxidizing atmosphere which is also employed in step (i).

The invention further provides a process for preparing maleic anhydride by heterogeneously catalyzed gas-phase oxidation of a hydrocarbon having at least four carbon atoms by means of oxygen-comprising gases using the catalyst of the invention. Shell-and-tube reactors are generally used as reactors. Suitable shell-and-tube reactors are described, for example, in EP-B 1 261 424.

Suitable hydrocarbons for use in the process of the invention are aliphatic and aromatic, saturated and unsaturated hydrocarbons having at least four carbon atoms, for example 1,3-butadiene, 1-butene, cis-2-butene, trans-2-butene, n-butane, $C_4$ mixture, 1,3-pentadiene, 1,4-pentadiene, 1-pentene, cis-2-pentene, trans-2-pentene, n-pentane, cyclopentadiene, dicyclopentadiene, cyclopentene, cyclopentane, $C_5$ mixture, hexenes, hexanes, cyclohexane and benzene. Preference is given to using propane, 1-butene, cis-2-butene, trans-2-butene, n-butane, benzene or mixtures thereof, in particular propane, n-butane or benzene. Particular preference is given to using n-butane, for example as pure n-butane or as a component in n-butane-comprising gases and liquids. The n-butane used can, for example, originate from natural gas, from steam crackers or FCC plants.

The hydrocarbon is generally introduced in a quantity-regulated manner, i.e. with a defined amount per unit time being continually set. The hydrocarbon can be metered in in liquid or gaseous form. It is preferably metered in liquid form with subsequent vaporization before entering the shell-and-tube unit.

Oxidants used are oxygen-comprising gases such as air, synthetic air, a gas enriched with oxygen or "pure" oxygen, e.g. oxygen originating from a fractation of air. The oxygen-comprising gas is also added in a quantity-regulated manner.

The process of the invention is carried out at a temperature of from 250 to 500° C. The temperature mentioned is, regardless of the type of reactor, in each case the average temperature of the heat transfer medium. When n-butane is used as hydrocarbon starting material, the process of the invention is preferably carried out at a temperature of from 380 to 460° C. and particularly preferably from 380 to 440° C. When propane is used, the process of the invention is preferably carried out in the range from 250 to 350° C. When benzene is used, the process of the invention is preferably carried out in the range from 330 to 450° C.

The process of the invention is advantageously carried out isothermally with a temperature profile which increases over the length of the reactor or using a combination of a temperature which increases over the length of the reactor and an isothermal mode of operation.

The process of the invention is advantageously carried out at an oxygen partial pressure of from 0.6 bar to 50 bar, preferably from 2 bar to 50 bar, particularly preferably from 3 bar to 50 bar, in particular from 4 bar to 50 bar.

The hydrocarbon concentration of the feed stream fed to the reactor unit is from 0.5 to 10% by volume, preferably from 0.8 to 10% by volume, particularly preferably from 1 to 10% by volume and very particularly preferably from 2 to 10% by volume.

The hydrocarbon conversion per pass through the reactor is from 40 to 100%, preferably from 50 to 95%, particularly preferably from 70 to 95% and in particular from 85 to 95%, of the hydrocarbon in the feed stream.

In the process of the invention, a GHSV (gas hourly space velocity) of preferably from 2000 to 10 000 $h^{-1}$ and particularly preferably from 3000 to 8000 $h^{-1}$, based on the volume of the feed stream standardized to 0° C. and 0.1013 MPa abs and based on the reaction volume which is filled with catalyst or whose geometric surface is coated with catalyst, is preferably set via the amount of feed stream introduced into the reactor unit.

The process of the invention can be carried out in two preferred process variants, viz. the variant in a "single pass" and the variant with "recirculation". In a "single pass", maleic anhydride and optionally oxygenated hydrocarbon by-products are removed from the reactor discharge and the remaining gas mixture discharged from the process and optionally utilized thermally. In the case of "recirculation" maleic anhydride and optionally oxygenated hydrocarbon by-products are likewise removed from the reactor discharge and the remaining gas mixture, which comprises unreacted hydrocarbon, is recirculated in its entirety or in part to the reactor. A further variant of "recirculation" is removal of the unreacted hydrocarbon and recirculation thereof to the reactor.

The reaction products or the product stream can optionally be diluted by addition of materials which are inert under the reaction conditions, for example water or nitrogen, either at the end of the reactor or at the reactor outlet so as to give a nonexplosive product stream. Furthermore, a nonexplosive product stream can advantageously be achieved by means of a pressure stage. This product stream can then be worked up by means of conventional work-up units.

When n-butane is used, a volatile phosphorus compound is advantageously introduced into the gas in the process of the invention to ensure a long catalyst operating life and a further increase in the conversion, selectivity, yield, space velocity of the catalyst and space-time yield. Its concentration at the beginning, i.e. at the reactor inlet, is from 0.2 to 20 ppm by volume of the volatile phosphorus compound based on the total volume of the gas at the reactor inlet. Preference is given to a content of from 0.5 to 5% by volume. Volatile phosphorus compounds are all phosphorus-comprising compounds which are present in gaseous form in the desired concentration under the use conditions. Preference is given to using triethyl phosphate or trimethyl phosphate as volatile phosphorus compound.

The invention is illustrated by the accompanying drawings and the following examples.

FIG. 1 shows a view of a shaped catalyst body according to the invention having four internal holes.

Figure 2:
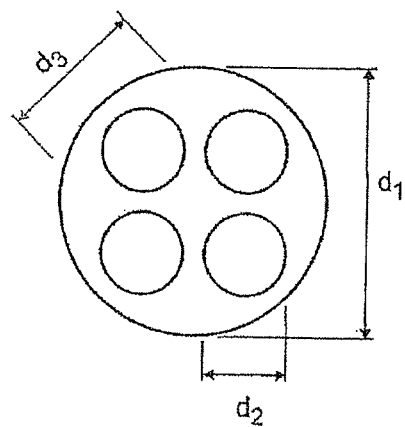
FIG. 2 shows a plan view of the shaped catalyst body depicted in FIG. 1.

FIG. 2 shows a plan view of the shaped catalyst body depicted in FIG. 1.

Definitions

The parameters used in this text are, unless indicated otherwise, defined as follows:

geometric surface area $A_{geo}$=geometric surface area of the shaped bodies on the basis of the geometric parameters $d_1$, h and $d_2$ [mm$^2$]

geometric volume $V_{geo}$=geometric volume of the shaped bodies on the basis of the geometric parameters $d_1$, h and $d_2$ [mm$^3$]

theoretical volume of solid cylinder $V_{overall}$=theoretical volume of a corresponding solid cylinder having a height h and an external diameter $d_1$ [mm$^3$]

$x_{n\text{-}butane}$=butane concentration of the feed stream $X_{n\text{-}butane}$=n-butane conversion $x_{TEP}$=triethyl phosphate concentration of the feed stream $x_{H2O}$=water vapor concentration of the feed stream GHSV=quantity of the feed stream, based on the volume standardized to 0° C. and 0.1013 MPa abs of the feed stream introduced and based on the reaction volume filled with catalyst tube fill density=bulk density of the catalyst in the reaction tube selectivity S (acrylic acid)=$n_{acrylic\ acid,reactor,out}/(n_{butane,reactor,in}-n_{butane,reactor,out})$ selectivity S (acetic acid)=$n_{acetic\ acid,reactor,out}/(n_{butane,reactor,in}-n_{butane,reactor,out})$ Determination of the residual isobutanol content in the dried catalyst precursor.

To determine the residual isobutanol content, about 4 g of the dried pulverulent catalyst precursor and about 10 g of N,N-dimethylformamide were weighed accurately into a heatable stirred apparatus provided with reflux condenser. The mixture was subsequently heated to the boiling point while stirring and maintained under these conditions for 30 minutes. After cooling, the suspension was filtered and the isobutanol content of the filtrate was determined quantitatively by gas chromatography. The residual isobutanol content was then calculated from the measured concentration of isobutanol in the N,N-dimethylformamide and the weighed out amounts of N,N-dimethylformamide and catalyst precursor.

Determination of the Lateral Compressive Strength of the Hollow Cylinders

To determine the lateral compressive strength, the shaped catalyst bodies were placed with the rounded side surface on in each case the flat material support plate of an appropriate measurement device in successive measurements. The two parallel flat end faces were thus oriented vertically. A flat metal punch was then driven down from the top onto the shaped catalyst body at an advance rate of 1.6 mm/min and the force applied to the shaped catalyst body was recorded as a function of time until fracture of the body occurred. The lateral compressive strength of the individual shaped catalyst bodies corresponds to the maximum force applied.

Determination of the Specific Pore Volume

The specific pore volume was determined by mercury porosimetry in accordance with DIN 66133.

Production of the Catalyst Precursor 6.1 m$^3$ of isobutanol were placed in a stirred 8 m$^3$ steel/enamel vessel which was blanketed with nitrogen, could be heated externally by means of pressurized water and was provided with baffles. After the three-stage impeller stirrer was started, the isobutanol was heated to 90° C. under reflux. At this temperature, the addition of 736 kg of vanadium pentoxide via the transport screw was commenced. After about ⅔ of the desired amount of vanadium pentoxide had been added after about 20 minutes, the introduction of 900 kg of 105% strength phosphoric acid by pumping was commenced while continuing to add vanadium pentoxide. To clear the pump, a further 0.2 m$^3$ of isobutanol were pumped in afterward. The reaction mixture was subsequently heated to about 100-108° C. under reflux and maintained under these conditions for 14 hours. The hot suspension was subsequently drained into a pressure filter which was blanketed with nitrogen and heated and the solid was filtered off at a temperature of about 100° C. at a pressure above the filter of up to 0.35 MPa abs. The filtercake was blown dry over a period of about one hour by continual introduction of nitrogen at 100° C. while stirring by means of a centrally arranged stirrer whose height could be adjusted. After blowing dry, the solid was heated to about 155° C. and evacuated to a pressure of 15 kPa abs (150 mbar abs). Drying was carried out to a residual isobutanol content of <2% by weight in the dried catalyst precursor.

The dried powder obtained was then heated for 2 hours in air in a rotary tube having a length of 6.5 m, an internal diameter of 0.9 m and internal helices. The speed of rotation of the rotary tube was 0.4 rpm. The powder was conveyed into the rotary tube in an amount of 60 kg/h. The inflow of air was 100 m$^3$/h. The temperatures of the five heating zones of equal length measured directly on the outside of the rotary tube were 250° C., 300° C., 340° C., 340° C. and 340° C. After cooling to room temperature, the catalyst precursor was intimately mixed with 1% by weight of graphite and compacted in a roller compactor. The fines having a particle size of <400 μm in the compacted material were sieved off and fed back to compacting. The coarse material having a particle size of 400 μm was intimately mixed with a further 2% by weight of graphite. This will hereinafter be referred to as "catalyst precursor powder".

Production of the Catalysts A, B and C

To produce the catalysts A and C, the catalyst precursor powder was mixed with 20% by weight of malonic acid. The catalyst precursor powder or the mixture with malonic acid was tableted in a tableting machine to produce 6.5×4.2×3.7 mm hollow cylinders (external diameter×height×diameter of the internal hole) (catalyst A) or 6.5×4.2 cylinders (external diameter×height) having four through-holes having a diameter of 1.85 (catalysts B and C). While pressing forces of about 10 kN were set during tableting of the hollow cylinder, about 8 kN suffice in the case of the shaped body having four internal holes.

The geometric properties of the shaped bodies are as follows:

| | | Catalysts | |
|---|---|---|---|
| | | A | B, C |
| $d_1$ | [mm] | 6.5 | 6.5 |
| h | [mm] | 4.2 | 4.2 |
| $d_2$ | [mm] | 3.7 | 1.85 |
| Number of holes | | 1 | 4 |
| External cylindrical surface | [mm$^2$] | 86 | 86 |
| End faces | [mm$^2$] | 22 | 22 |
| Internal cylindrical surface(s) | [mm$^2$] | 49 | 98 |
| $A_{geo}$ | [mm$^2$] | 157 | 206 |
| $V_{geo}$ | [mm$^3$] | 94 | 94 |
| $A_{geo}/V_{geo}$ | [mm$^{-1}$] | 1.67 | 2.18 |
| $V_{overall}$ | [mm$^3$] | 139 | 139 |
| $V_{geo}/V_{overall}$ | % | 68 | 68 |

The tableted catalyst precursor specimens (green bodies) were subsequently introduced into a belt calciner and calcined as follows, with the residence time in each calcination zone being about 1.78 h:

Preactivation Parameters for Catalysts A and C (with Malonic Acid)

| Zone | Temperature | Fresh gas introduced |
|---|---|---|
| Calcination zone 1 | 150° C. | Air |
| Calcination zone 2 | 180° C. | Air |
| Calcination zone 3 | 280° C. | Air, N$_2$/H$_2$O vapor (5% by volume of O$_2$) |
| Calcination zone 4 | 325° C. | Air, N$_2$/H$_2$O vapor (5% by volume of O$_2$) |
| Transition zone | Cooling to 200° C. | |
| Calcination zone 5 | 335° C. | N$_2$ |
| Calcination zone 6 | 400° C. | N$_2$/H$_2$O vapor (1:1) |
| Calcination zone 7 | 425° C. | N$_2$/H$_2$O vapor (1:1) |
| Calcination zone 8 | 355° C. | N$_2$ |

Preactivation Parameters for Catalyst B (without Pore Former)

| Zone | Temperature | Fresh gas introduced |
|---|---|---|
| Calcination zone 1 | 140° C. | Air |
| Calcination zone 2 | 140° C. | Air |
| Calcination zone 3 | 260° C. | Air |
| Calcination zone 4 | 300° C. | Air |
| Transition zone | Cooling to 200° C. | Air |
| Calcination zone 5 | 335° C. | N$_2$ |
| Calcination zone 6 | 400° C. | N$_2$/H$_2$O vapor (1:1) |
| Calcination zone 7 | 425° C. | N$_2$/H$_2$O vapor (1:1) |
| Calcination zone 8 | 355° C. | N$_2$ |

Catalytic Tests

The test plant was equipped with a feed unit and a reactor tube. Replacement of a shell-and-tube reactor by a reactor tube is very readily possible on the laboratory or pilot plant scale as long as the dimensions of the reactor tube are in the region of those of an industrial reactor tube. The plant was operated in a "single pass".

The hydrocarbon was introduced in liquid form in a quantity-regulated manner by means of a pump. As oxygen-comprising gas, air was introduced in a quantity-regulated manner. Triethyl phosphate (TEP) was likewise introduced in a quantity-regulated manner, in liquid form dissolved in water.

The shell-and-tube reactor unit comprised a shell-and-tube reactor having one reactor tube. The length of the reactor tube was 6.5 m, and the internal diameter was 22.3 mm. A multi-thermocouple having 20 temperature measuring points was located in a protective tube having an external diameter of 6 mm within the reactor tube. Heating of the reactor was effected by means of a heat transfer medium circuit having a length of 6.5 m. A salt melt was used as heat transfer medium. The reaction gas mixture flowed from the top downward through the reactor tube. The upper 0.2 m of the 6.5 m long reactor tube remained unfilled. This was followed by a 0.3 m long preheating zone filled with shaped steatite bodies as inert material. The preheating zone was followed by the catalyst bed which comprised a total of 2173 ml of catalyst.

Gaseous product was taken off immediately downstream of the shell-and-tube reactor unit and passed to gas-chromatographic on-line analysis. The main stream of the gaseous reactor discharge was discharged from the plant.

The reaction conditions for catalytic testing were as follows: $x_{n-butane}$=2% by volume, GHSV=2000 h$^{-1}$, $P_{in}$=2.3 barg, $X_{n-butane}$=85%, $x_{TEP}$=2.25-2.5 ppm by volume, $x_{H2O}$=3% by volume.

The measurements were carried out after a minimum running time of the catalyst of 370 h.

TABLE

Characterization results for the three catalysts

| | | Catalyst | | |
|---|---|---|---|---|
| | | A | B | C |
| Green body | | | | |
| Lateral compressive strength at narrow point* | [N] | 14.1 | 5.6 | 11.8 |
| Lateral compressive strength at web** | [N] | | 59 | 61 |
| Density | [g/ml] | 1.69 | 1.55 | 1.57 |
| Preactivation | | | | |
| T$_{max}$ | [° C.] | 390 | 380 | 390 |
| t$_{Tmax}$ | [min] | 1 | 0 | 1 |
| Catalyst | | | | |
| Lateral compressive strength at narrow point* | [N] | 11.4 | 8 | 8 |
| Lateral compressive strength at web** | [N] | | 35 | 29 |
| Density | [g/ml] | 1.35 | 1.44 | 1.29 |
| V$_{Ox}$ | | 4.18 | 4.18 | 4.16 |
| Pore volume (PV) | [ml/g] | 0.368 | 0.336 | 0.408 |
| Catalyst testing | | | | |
| Tube fill weight | [g/l] | 442 | 458 | 417 |
| MAn yield | [mol %] | 54.5 | 57.9 | 58.9 |
| MAn yield | [m/m %] | 95.5 | 97.9 | 99.0 |
| Selectivity to acrylic acid | [mol %] | 1.02 | 1.16 | 1.12 |
| Selectivity to acetic acid | [mol %] | 1.22 | 1.21 | 1.34 |
| Salt bath temperature | [° C.] | 406 | 410 | 405 |

*Lateral compressive strength at narrow point: the shaped body was placed in the apparatus for testing the lateral compressive strength in such a way that the shaped body diameter in the direction of the applied force comprised two full internal holes.
**Lateral compressive strength at web: the shaped body was placed in the apparatus for determining the lateral compressive strength in such a way that the shaped body diameter in the direction of the applied force comprised no internal holes.

The results show that the catalysts B and C having four internal holes led to a significant increase in the MAn yield, with the use of a pore former (catalyst C) leading to a further increase in yield. It is surprising that the catalyst C displayed the lowest tube fill weight, i.e. a higher yield was achieved using a smaller amount of catalyst. The lateral compressive strengths achieved for the catalysts B and C are satisfactory for practical requirements.

The invention claimed is:

1. A shaped catalyst body for preparing maleic anhydride by gas-phase oxidation of a hydrocarbon having at least four carbon atoms where the shaped catalyst body comprises a catalytically active composition comprising vanadium, phosphorus and oxygen, has an essentially cylindrical body having a longitudinal axis, wherein the cylindrical body has at least two parallel internal holes which are essentially parallel to the cylinder axis of the body and go right through the body, and wherein the internal holes have a round or oval cross section.

2. The shaped catalyst body according to claim 1, wherein the central axes of the internal holes are located equidistantly on a cylindrical surface which is concentric with the surface of the cylindrical body.

3. The shaped catalyst body according to claim 1, wherein the cylindrical body has four internal holes.

4. The shaped catalyst body according to claim 1, wherein the sum of the surfaces of the internal holes is equal to or greater than the external surface of the cylindrical body.

5. The shaped catalyst body according to claim 1, wherein both the smallest distance between the internal holes and the smallest distance between the internal holes and the outer cylindrical surface of the body is in each case at least 6% of the diameter of the cylindrical body.

6. The shaped catalyst body according to claim 1, wherein the ratio of the geometric surface $A_{geo}$ to the geometric volume $V_{geo}$ is at least 2.0 $mm^{-1}$.

7. The shaped catalyst body according to claim 1, wherein the ratio of the geometric volume $V_{geo}$ of the cylindrical body to the theoretical volume $V_{overall}$ of a corresponding solid cylinder having the same height h and the same external diameter $d_1$ is not more than 0.85.

8. The shaped catalyst body according to claim 1, wherein the external diameter $d_1$ of the cylindrical body is from 3 to 10 mm, the height h of the cylindrical body is from 1 to 10 mm and the diameter of each internal hole $d_2$ is from 0.5 to 4 mm.

9. The shaped catalyst body according to claim 1, wherein the shaped catalyst body is porous.

10. The shaped catalyst body according to claim 9, wherein the shaped catalyst body has a specific pore volume of at least 0.30 ml/g.

11. The shaped catalyst body according to claim 1, wherein the cylindrical body has from two to five internal holes.

* * * * *